United States Patent
Abeywardane et al.

(10) Patent No.: US 8,969,348 B2
(45) Date of Patent: Mar. 3, 2015

(54) CHYMASE INHIBITORS

(75) Inventors: Asitha Abeywardane, Danbury, CT (US); Ming-Hong Hao, Ridgefield, CT (US); Steven John Taylor, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 166 days.

(21) Appl. No.: 13/058,624

(22) PCT Filed: Aug. 5, 2009

(86) PCT No.: PCT/US2009/052773
§ 371 (c)(1),
(2), (4) Date: Apr. 5, 2011

(87) PCT Pub. No.: WO2010/019417
PCT Pub. Date: Feb. 18, 2010

(65) Prior Publication Data
US 2012/0129863 A1    May 24, 2012

Related U.S. Application Data

(60) Provisional application No. 61/088,551, filed on Aug. 13, 2008.

(51) Int. Cl.
*A01N 43/58* (2006.01)
*A61K 31/495* (2006.01)
*C07D 237/00* (2006.01)

(52) U.S. Cl.
USPC ................ 514/248; 514/247; 544/237

(58) Field of Classification Search
USPC ................ 544/237; 514/247, 248
See application file for complete search history.

(56) References Cited

U.S. PATENT DOCUMENTS 3,813,384 A * 5/1974 Vogelsang ............ 540/599
5,380,721 A * 1/1995 Johnson et al. ............ 514/183
5,464,838 A * 11/1995 Kutscher et al. ............ 514/248
6,329,370 B1 * 12/2001 Napoletano et al. ....... 514/234.5

FOREIGN PATENT DOCUMENTS

| DE | 4207234 A1 | 9/1993 |
| DE | 3813531 A1 | 11/1998 |
| EP | 0475527 A2 | 3/1992 |
| EP | 597540 A1 | 5/1994 |
| JP | S62252774 A | 11/1987 |
| JP | H06220025 A | 8/1994 |
| JP | 2002521370 A | 7/2002 |
| JP | 2003535850 A | 12/2003 |
| WO | 00/05218 A1 | 2/2000 |
| WO | 01/94319 A1 | 12/2001 |
| WO | 2008/023357 A1 | 2/2008 |
| WO | 2008/074803 A2 | 6/2008 |

OTHER PUBLICATIONS

Kidwai et al., New indolyl phthalazinones and phthalazine derivatives as spermicidal agents Acta Pharmaceutica (Zagreb) (1997), 47(1), 53-57 CODEN: ACPHEE; ISSN: 1330-0075; English.*

Del Olmo et al., Vasorelaxant activity of phthalazinones and related compounds Bioorganic & Medicinal Chemistry Letters (2006), 16(10), 2786-2790 CODEN: BMCLE8; ISSN: 0960-894X; English.*

Abdel-Fatah et al., Synthesis of certain phthalazine derivatives of 1,3,4-oxadiazoles and s-triazolothiadiazines of possible antimicrobial activities Egyptian Journal of Pharmaceutical Sciences (1988), 29(1-4), 259-68 CODEN: EJPSBZ; ISSN: 0301-5068; English.*

Ziebarth et al., Formation of the carcinogen N-nitrosodimethylamine from drugs and nitrite under simulated human gastric conditions, Hommage Professeur Rene Truhaut (1984), 1234-7 Publisher: Fac. Pharm. Univ. Paris, Paris, Fr. CODEN: 55HVAS.*

Dusemund et al., Isoquinolino[3,2-a]phthalazine-5,8-diones Archiv der Pharmazie (Weinheim, Germany) (1982), 315(11), 925-30 CODEN: ARPMAS; ISSN: 0365-6233; German.*

International Search Report dated Jun. 21, 2010, for corresponding PCT Application No. PCT/US09/52773 filed on Aug. 5, 2009; and Written Opinion dated Jun. 21, 2010.

del Olmo, Ester et al. "Vasorelaxant activity of phthalazinones and related compounds" (2006) Bioorganic & Medicinal Chemistry Letters 16, pp. 2786-2790.

Abdel-Fattah, B. et al. "Synthesis of Certain Phthalazine Derivates of 1,3,4-Oxadiazoles and s-Triazolothiadiazines of Possible Antimicrobial Activities" Egyptian Journal of Pharmaceutical Sciences (1988) 29 (1-4) ISSN: 0301-5068.

RN 114897-85-7. Index Name: 2(1H)-Phthalazineacetic acid, 1-oxo-4-(phenylmethyl); Entered STN: Jun. 18, 1988.

RN 132544-84-4. Index Name: 2(1H)-Phthalazineacetic acid, 1-oxo-4-(phenylmethyl)-ethyl ester; Entered STN: Mar. 8, 1991.

(Continued)

*Primary Examiner* — Paul V. Ward
(74) *Attorney, Agent, or Firm* — Michael P. Morris; Usha R. Patel

(57) ABSTRACT

Disclosed are small molecule inhibitors which are useful in treating various diseases and conditions involving chymase.

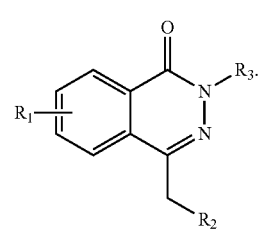

(I)

Also disclosed are pharmaceutical compositions, methods of using and making the same.

3 Claims, No Drawings

(56) References Cited

OTHER PUBLICATIONS

RN 37740-39-9. Index Name: 2 (1H)-Phthalazinepropanoic acid, 1-oxo-4-(phenylmethyl); Entered STN: Nov 16, 1984.

Yamaguchi, Masahisa et al. "Novel Antiasthmatic Agents with Dual Activities of Thromboxane A2 Synthetase Inhibition and Bronchodilation. 1.2-[2-(1-Imidazolyl)alkyl]-1 (2H)-phthalazinones" J. Med. Chem. (1993) vol. 36, pp. 4052-4060.

Yamaguchi, Masahisa et al. "Novel Antiasthmatic Agents with Dual Activities of Thromboxane A2 Synthetase Inhibition and Bronchodilation. IV. 2-[2-(1-Imidazolyl)ethyl]-4-(3-pyridyl)-1 (2H)-phthalazinones" Chem. Pharm. Bull. (1994) vol. 42 No. 9, pp. 1850-1853.

* cited by examiner

CHYMASE INHIBITORS

APPLICATION DATA

This application claims benefit to U.S. provisional application Ser. No. 61/088,551 filed Aug. 13, 2008.

FIELD OF THE INVENTION

The invention relates to small molecule inhibitors which are useful in treating various diseases and conditions involving Chymase.

BACKGROUND OF THE INVENTION

In cardiac tissue of cardiomyopathic patients, transforming growth factor-β (TGF-β), which has been demonstrated to stimulate cardiac fibrosis in animal models (Kuwahara, et al. Circulation, 2002, 106, 130), is increased (Li et al., Circulation, 1997, 96, 874). In the myocardial fibrotic area, it is known that mast cells are increased in number and may contribute to the development of fibroblast proliferation in cardiac tissues of patients with cardiomyopathy (Patella et al., Circulation, 1998, 97, 971). Chymase is a chymotrypsin-like serine protease contained in the secretory granules of mast cells. Although the precise physiological roles of Chymase have not been completely revealed, Chymase is known to transform angiotensin I to angiotensin II and may contribute to activation of TGF-13, matrix proteases, and cytokines (Taipale et al., J. Biol. Chem., 1995, 270, 4689; Takai et al., Life Sci., 1996, 58, 591; Takai et al., Circulation, 1999, 100, 654).

A potent and selective Chymase inhibitor may have potential use as a treatment of chronic heart failure, atherosclerosis, restenosis, and myocardial infarction by inhibiting local production of angiotensin II in the heart and release of TGF-β, two independent mediators of cardiac remodeling. An inhibitor may also have potential use for treatment of mast cell mediated diseases such as dermatitis, asthma, chronic obstructive pulmonary disease (COPD), and pulmonary inflammation, since Chymase is implicated in microvascular leakage, neutrophil accumulation, the stimulation of mucus secretion, and the modulation of cytokines (He et al., Eur. J. Pharmacol., 1998, 352, 91).

Several small molecule Chymase inhibitors have been reported to be efficacious in the cardiomyopathic hamster model of heart failure (Takai et al. J. Pharmacol. Exp. Ther. 2003, 305, 17), in carotid artery injury by a balloon catheter in dogs (Takai et al. J. Pharmacol. Exp. Ther, 2003, 304, 841), and in the hamster left anterior descending coronary artery ligation model of heart failure (WO 03/018061). Additionally, a Chymase inhibitor has been demonstrated to be efficacious in a sheep asthma model (WO 2005/073214). However, there is no example of commercialization of a Chymase inhibitor as a medicament.

SUMMARY OF THE INVENTION

It is therefore an object of the invention to provide a small molecule a Chymase inhibitor as defined herein, and pharmaceutical compositions thereof.

It is also an object of the invention to provide methods of using said Chymase inhibitors to treat various diseases and conditions related thereto.

It is a further object of the invention to provide processes of preparing said Chymase inhibitors.

DETAILED DESCRIPTION OF THE INVENTION

In one generic aspect of the invention, there is provided a compound of the formula (I):

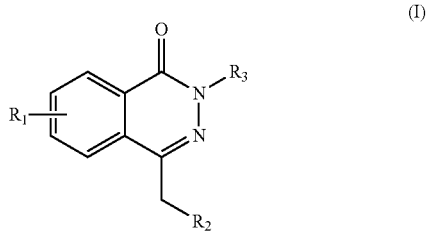

wherein:

$R_1$ is hydrogen, $C_1$-$C_5$ linear or branched alkyl group, $C_1$-$C_5$ linear or branched alkoxy group or halogen;

$R_2$ is aryl or heteroaryl group optionally independently substituted with one to three substituents chosen from halogen, hydroxyl, $C_1$-$C_5$ linear or branched alkyl, $C_1$-$C_5$ linear or branched alkoxy, $C_1$-$C_5$ linear or branched alkylthio and oxo;

$R_3$ is $C_1$-$C_5$ linear or branched alkyl group optionally independently substituted with one to three substituents chosen from $C_1$-$C_5$ linear or branched alkyl, carboxyl, $C_1$-$C_5$ linear or branched alkoxycarbonyl, carboxamido (wherein the N atom is substituted with alkylsulfonyl group) heteroaryl (optionally substituted with hydroxyl) and aryl;

or a pharmaceutically acceptable salt thereof.

In another embodiment there is provided a compound according to the embodiment immediately above and wherein:

$R_1$ is hydrogen or halogen;

$R_2$ is phenyl substituted with $C_1$-$C_5$ linear or branched alkyl or $C_1$-$C_5$ linear or branched alkoxy, naphthyl, indolyl or azaindolyl group each naphthyl, indolyl or azaindolyl optionally independently substituted with one to three substituents chosen from halogen, $C_1$-$C_5$ linear or branched alkyl or $C_1$-$C_5$ linear or branched alkoxy;

$R_3$ is $C_1$-$C_5$ linear or branched alkyl group optionally substituted with one to three substituents chosen from $C_1$-$C_5$ linear or branched alkyl, carboxyl and aryl.

In another embodiment there is provided a compound according to the embodiment immediately above and wherein:

$R_1$ is hydrogen;

$R_2$ is naphthyl or indolyl group each optionally independently substituted with one to three $C_1$-$C_5$ linear or branched alkyl groups;

$R_3$ is $C_1$-$C_3$ linear or branched alkyl group optionally substituted with one to three substituents chosen from $C_1$-$C_3$ linear or branched alkyl, carboxyl and phenyl.

In a further embodiment there is provided a compound according to the embodiment immediately above and wherein:

$R_2$ is naphthyl or indolyl group each optionally substituted with one to two methyl groups $R_3$ is $C_1$-$C_2$ linear alkyl group substituted with one to three substituents chosen from $C_1$-$C_3$ linear or branched alkyl, carboxyl and phenyl.

In another generic aspect of the invention, there is provided a compound of the formula (II):

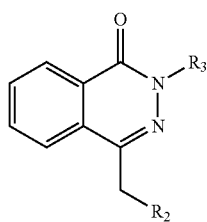

(II)

wherein for the Formula (II), the component

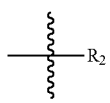

is chosen from B1-B6 in the table I below;
and component

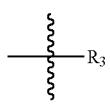

is chosen from C1-C5 in the table I below;

TABLE I

| | -R₂ | | -R₃ |
|---|---|---|---|
| B1 | indol-3-yl | C1 | -CH(CH₃)CH₂COOH |
| B2 | 1-methylindol-3-yl | C2 | -CH(CH₃)CH₂CH₂COOH |
| B3 | 1,4-dimethylindol-3-yl | C3 | -CH(CH₃)CH(C₃H₇)COOH |

TABLE I-continued

| | -R₂ | | -R₃ |
|---|---|---|---|
| B4 | naphthalen-1-yl | C4 | -C(CH₃)(Ph)COOH |
| B5 | 2,5-dimethylphenyl | C5 | -CH(CH₃)CH(C₃H₇)COOEt |
| B6 | 5-methoxy-1H-indol-3-yl | | | or a pharmaceutically acceptable salt thereof.

In another embodiment of the invention there is provided the following compounds, in table II, which can be made according to the general synthetic procedures and examples which follow:

Table II

| Structure | Name |
|---|---|
| 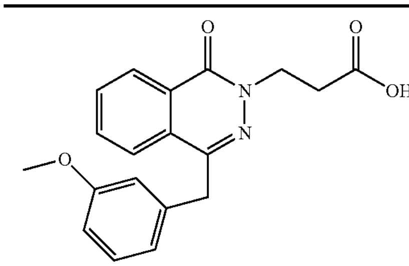 | 3-[4-(3-Methoxybenzyl)-1-oxophthalazin-2(1H)-yl] propanoic acid |
| 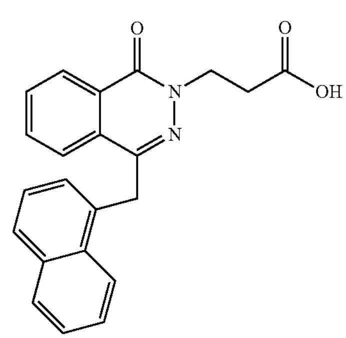 [SMILES: O=C(O)CCn1nc(Cc2cccc3ccccc23)c2ccccc2c1=O] | 3-[4-(Naphthalen-1-ylmethyl)-1-oxophthalazin-2(1H)-yl] propanoic acid |

Table II-continued

| Structure | Name |
|---|---|
| 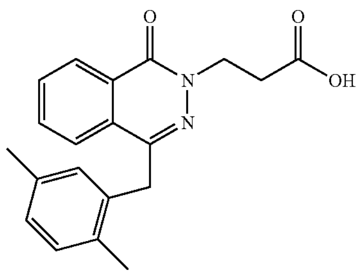 [SMILES: Cc1ccc(C)c(Cc2nn(CCC(=O)O)c(=O)c3ccccc23)c1] | 3-[4-(2,5-Dimethylbenzyl)-1-oxophthalazin-2(1H)-yl]propanoic acid |
| 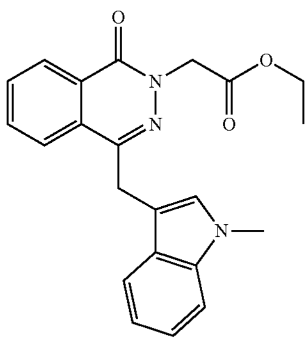 [SMILES: CCOC(=O)Cn1nc(Cc2cn(C)c3ccccc23)c2ccccc2c1=O] | Ethyl {4-[(1-methyl-1H-indol-3-yl)methyl]-1-oxophthalazin-2(1H)-yl}acetate |
| 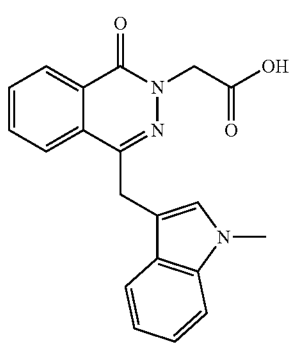 [SMILES: Cn1cc(Cc2nn(CC(=O)O)c(=O)c3ccccc23)c2ccccc21] | {4-[(1-Methyl-1H-indol-3-yl)methyl]-1-oxophthalazin-2(1H)-yl}acetic acid |
| 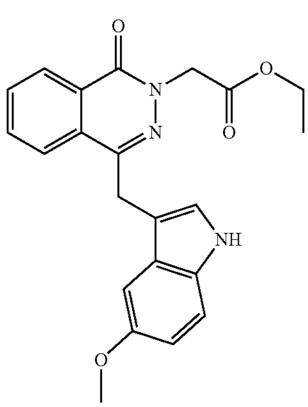 [SMILES: CCOC(=O)Cn1nc(Cc2c[nH]c3ccc(OC)cc23)c2ccccc2c1=O] | Ethyl {4-[(5-methoxy-1H-indol-3-yl)methyl]-1-oxophthalazin-2(1H)-yl}acetate |
| | Ethyl [4-(1H-indol-3-ylmethyl)-1-oxophthalazin-2(1H)-yl]acetate |
| | tert-Butyl 3-[4-(1H-indol-3-ylmethyl)-1-oxophthalazin-2(1H)-yl]propanoate |
| | tert-Butyl 3-{4-[(1-methyl-1H-indol-3-yl)methyl]-1-oxophthalazin-2(1H)-yl}propanoat |
| | {4-[(1,4-Dimethyl-1H-indol-3-yl)methyl]-1-oxophthalazin-2(1H)-yl}acetic acid |

Table II-continued

| Structure | Name |
|---|---|
| 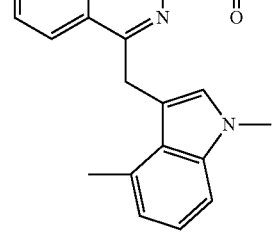 | Ethyl {4-[(1,4-dimethyl-1H-indol-3-yl)methyl]-1-oxophthalazin-2(1H)-yl}acetate |
| 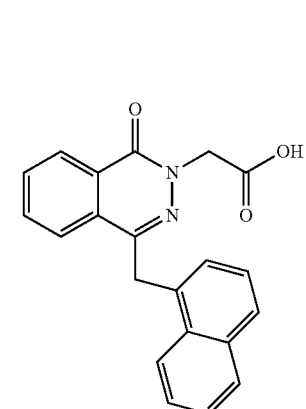 | [4-(Naphthalen-1-yl methyl)-1-oxophthalazin-2(1H)-yl] acetic acid |
| 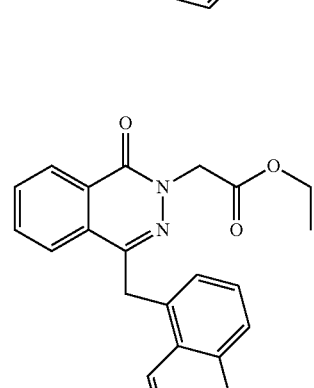 | Ethyl [4-(naphthalen-1-yl methyl)-1-oxophthalazin-2(1H)-yl]acetate |
| 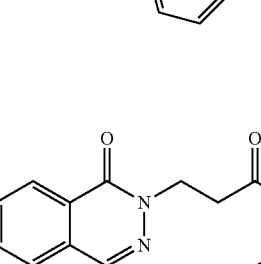 | tert-Butyl 3-{4-[(1,4-dimethyl-1H-indol-3-yl)methyl]-1-oxophthalazin-2(1H)-}propanoate |

Table II-continued

| Structure | Name |
|---|---|
| 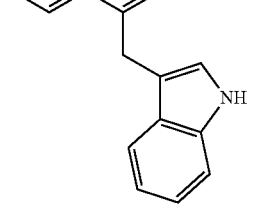 | [4-(1H-indol-3-ylmethyl)-1-oxophthalazin-2(1H)-yl] acetic acid |
| 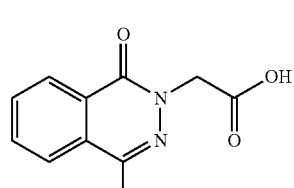 | {4-[(5-Methoxy-1H-indol-3-yl) methyl]-1-oxophthalazin-2(1H)-yl} acetic acid |
| 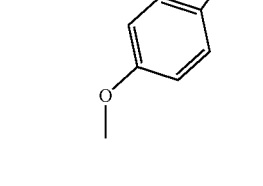 | 3-{4-[(1,4-Dimethyl-1H-indol-3-yl)methyl]-1-oxophthalazin-2(1H)-yl} propanoic acid |
| 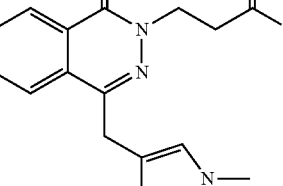 | 3-[4-(1H-indol-3-ylmethyl)-1-oxophthalazin-2(1H)-yl] propanoic acid |

Table II-continued

| Structure | Name |
|---|---|
| 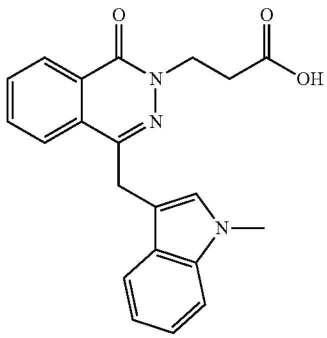 [SMILES: Cn1cc(Cc2nn(CCC(=O)O)c(=O)c3ccccc23)c2ccccc21] | 3-{4-[(1-Methyl-1H-indol-3-yl)methyl]-1-oxophthalazin-2(1H)-yl}propanoic acid |
| 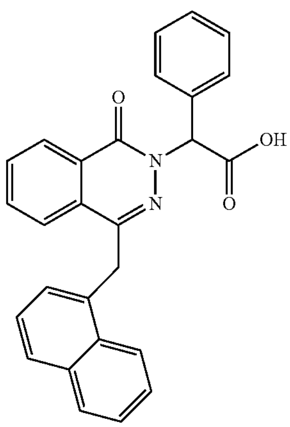 [SMILES: O=C(O)C(c1ccccc1)n1nc(Cc2cccc3ccccc23)c2ccccc2c1=O] | [4-(Naphthalen-1-yl-methyl)-1-oxophthalazin-2(1H)-yl](phenyl)acetic acid |
| 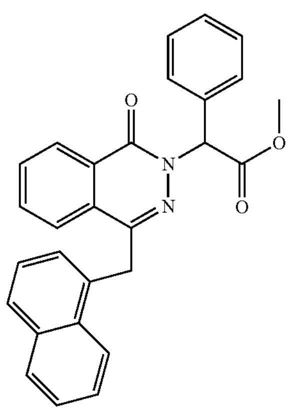 [SMILES: COC(=O)C(c1ccccc1)n1nc(Cc2cccc3ccccc23)c2ccccc2c1=O] | Methyl[4-(naphthalen-1-yl-methyl)-1-oxophthalazin-2(1H)-yl](phenyl)acetate |
| 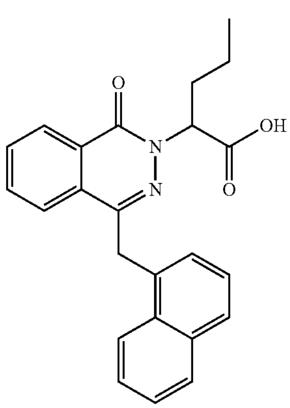 [SMILES: CCCC(C(=O)O)n1nc(Cc2cccc3ccccc23)c2ccccc2c1=O] | 2-[4-(Naphthalen-1-yl-methyl)-1-oxophthalazin-2(1H)-yl]pentanoic acid |
|  | Ethyl 2-[4-(naphthalen-1-yl-methyl)-1-oxophthalazin-2(1H)-yl]pentanoate |
|  | Methyl {4-[(1-methyl-1H-indol-3-yl)methyl]-1-oxophthalazin-2(1H)-yl}(phenyl)acetate |
|  | {4-[(1-Methyl-1H-indol-3-yl)methyl]-1-oxophthalazin-2(1H)-yl}(phenyl)acetic acid |
|  | Ethyl 2-{4-[(1,4-dimethyl-1H-indol-3-yl)methyl]-1-oxophthalazin-2(1H)-yl}pentanoate |

Table II-continued

| Structure | Name |
|---|---|
| 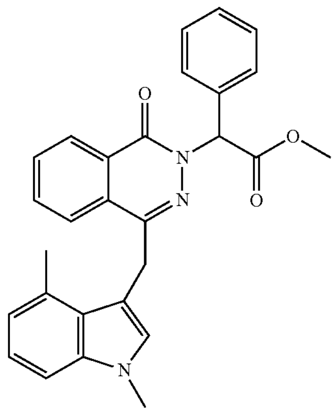 [SMILES: COC(=O)C(c1ccccc1)n1nc(Cc2cn(C)c3cccc(C)c23)c2ccccc2c1=O] | Methyl {4-[(1,4-dimethyl-1H-indol-3-yl)methyl]-1-oxophthalazin-2(1H)-yl}(phenyl)acetate |
| 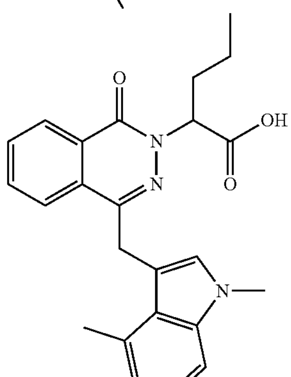 | 2-{4-[(1,4-Dimethyl-1H-indol-3-yl)methyl]-1-oxophthalazin-2(1H)-yl}pentanoic acid |
| 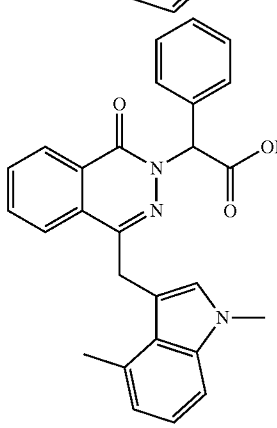 | {4-[(1,4-Dimethyl-1H-indol-3-yl)methyl]-1-oxophthalazin-2(1H)-yl}(phenyl)acetic acid |
| 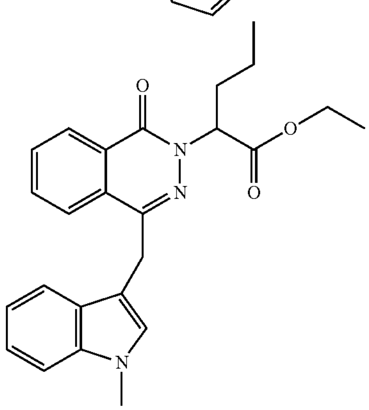 | Ethyl 2-{4-[(1-methyl-1H-indol-3-yl)methyl]-1-oxophthalazin-2(1H)-yl}pentanoate |
| | 2-{4-[(1-Methyl-1H-indol-3-yl)methyl]-1-oxophthalazin-2(1H)-yl}pentanoic acid |
| | 4-(1,4-Dimethyl-1H-indol-3-ylmethyl)-2-(1H-tetrazol-5-ylmethyl-2H-phthalazin-1-one |
| | 4-(1,4-Dimethyl-1H-indol-3-ylmethyl)-2-(3-hydroxy-isoxazol-5-ylmethyl)-2H-phthalazin-1-one |
| | N-{2-[4-(4-Methyl-1H-indol-3-ylmethyl)-1-oxo-1H-phthalazin-2-yl]-acetyl}-methanesulfonamide | or a pharmaceutically acceptable salt thereof.

In another embodiment of the invention there is provided the following compounds, in table III, which showed inhibitory activity in the Chymase assay:

TABLE III

| Structure | Name |
|---|---|
| 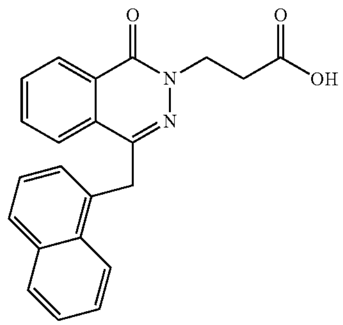 [SMILES: O=C(O)CCn1nc(Cc2cccc3ccccc23)c2ccccc2c1=O] | 3-[4-(Naphthalen-1-ylmethyl)-1-oxophthalazin-2(1H)-yl]propanoic acid |
| 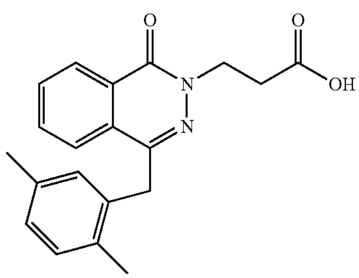 [SMILES: Cc1ccc(C)c(Cc2nn(CCC(=O)O)c(=O)c3ccccc23)c1] | 3-[4-(2,5-Dimethylbenzyl)-1-oxophthalazin-2(1H)-yl]propanoic acid |
| 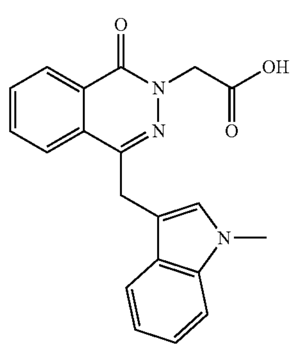 [SMILES: Cn1cc(Cc2nn(CC(=O)O)c(=O)c3ccccc23)c2ccccc21] | {4-[(1-Methyl-1H-indol-3-yl)methyl]-1-oxophthalazin-2(1H)-yl}acetic acid |
| 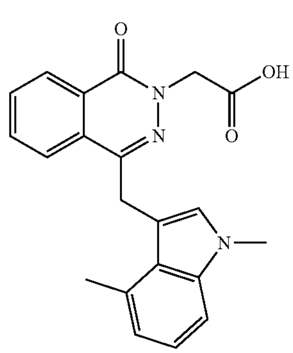 [SMILES: Cc1cccc2c1c(Cc1nn(CC(=O)O)c(=O)c3ccccc13)cn2C] | {4-[(1,4-Dimethyl-1H-indol-3-yl)methyl]-1-oxophthalazin-2(1H)-yl}acetic acid |

TABLE III-continued

| Structure | Name |
|---|---|
| 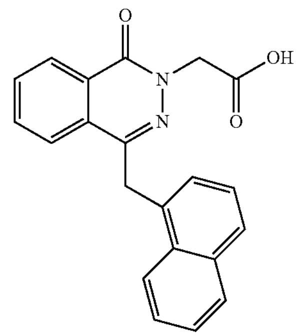 [SMILES: O=C(O)Cn1nc(Cc2cccc3ccccc23)c2ccccc2c1=O] | [4-(Naphthalen-1-ylmethyl)-1-oxophthalazin-2(1H)-yl]acetic acid |
| 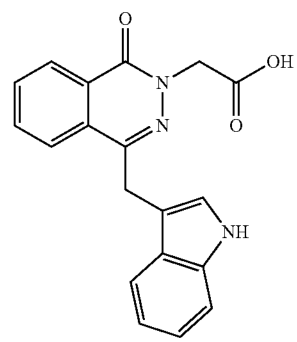 [SMILES: O=C(O)Cn1nc(Cc2c[nH]c3ccccc23)c2ccccc2c1=O] | [4-(1H-indol-3-ylmethyl)-1-oxophthalazin-2(1H)-yl]acetic acid |
| 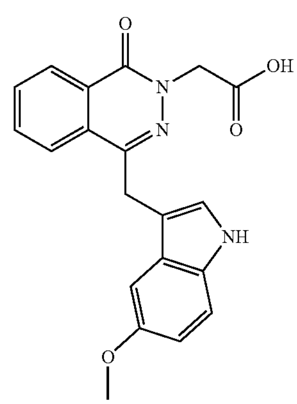 [SMILES: COc1ccc2[nH]cc(Cc3nn(CC(=O)O)c(=O)c4ccccc34)c2c1] | {4-[(5-Methoxy-1H-indol-3-yl)methyl]-1-oxophthalazin-2(1H)-yl}acetic acid |
| 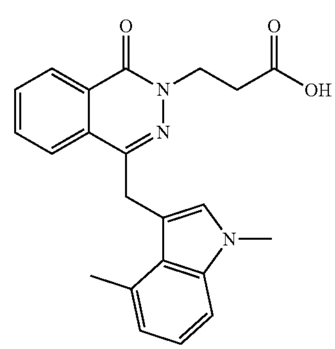 [SMILES: Cc1cccc2c1c(Cc1nn(CCC(=O)O)c(=O)c3ccccc13)cn2C] | 3-{4-[(1,4-Dimethyl-1H-indol-3-yl)methyl]-1-oxophthalazin-2(1H)-yl}propanoic acid |

TABLE III-continued

| Structure | Name |
|---|---|
| 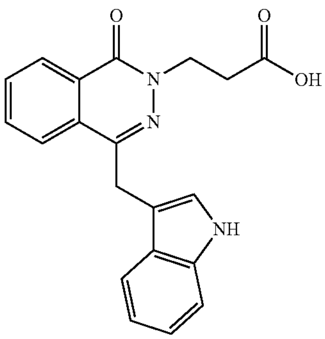 [SMILES: O=C(O)CCn1nc(Cc2c[nH]c3ccccc23)c2ccccc2c1=O] | 3-[4-(1H-indol-3-ylmethyl)-1-oxophthalazin-2(1H)-yl]propanoic acid |
| 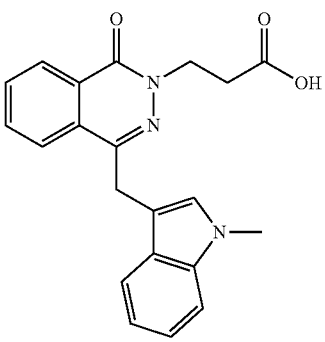 [SMILES: Cn1cc(Cc2nn(CCC(=O)O)c(=O)c3ccccc23)c2ccccc21] | 3-{4-[(1-Methyl-1H-indol-3-yl)methyl]-1-oxophthalazin-2(1H)-yl}propanoic acid |
| 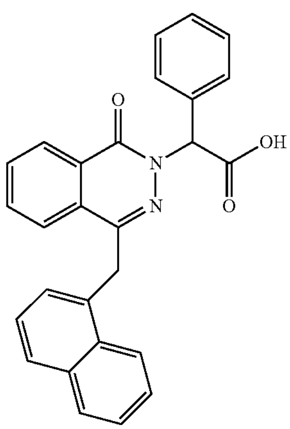 [SMILES: O=C(O)C(c1ccccc1)n1nc(Cc2cccc3ccccc23)c2ccccc2c1=O] | [4-(Naphthalen-1-ylmethyl)-1-oxophthalazin-2(1H)-yl](phenyl)acetic acid |
| 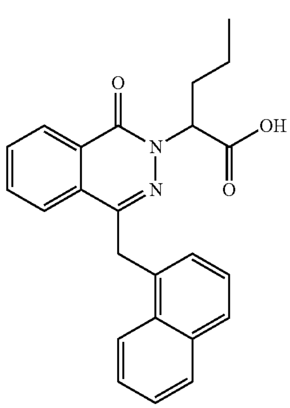 [SMILES: CCCC(C(=O)O)n1nc(Cc2cccc3ccccc23)c2ccccc2c1=O] | 2-[4-(Naphthalen-1-ylmethyl)-1-oxophthalazin-2(1H)-yl]pentanoic acid |
| 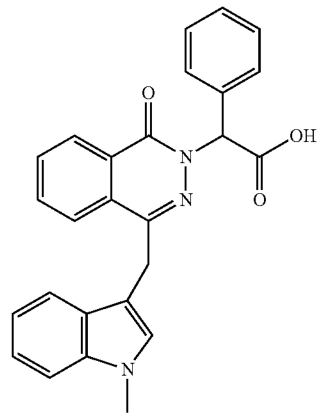 [SMILES: Cn1cc(Cc2nn(C(C(=O)O)c3ccccc3)c(=O)c3ccccc23)c2ccccc21] | {4-[(1-Methyl-1H-indol-3-yl)methyl]-1-oxophthalazin-2(1H)-yl}(phenyl)acetic acid |
| 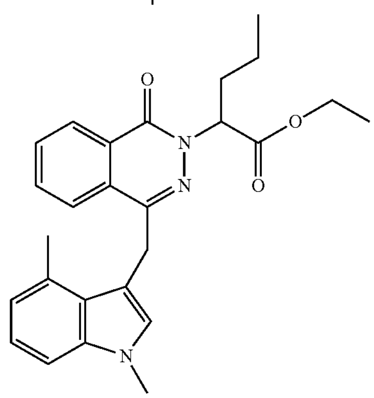 | Ethyl 2-{4-[(1,4-dimethyl-1H-indol-3-yl)methyl]-1-oxophthalazin-2(1H)-yl}pentanoate |
| 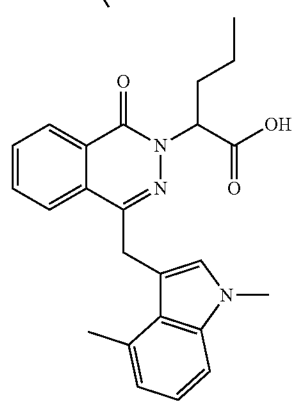 | 2-{4-[(1,4-Dimethyl-1H-indol-3-yl)methyl]-1-oxophthalazin-2(1H)-yl}pentanoic acid |
| 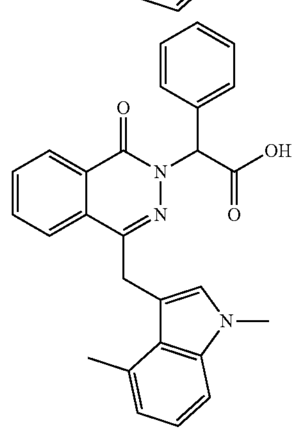 | {4-[(1,4-Dimethyl-1H-indol-3-yl)methyl]-1-oxophthalazin-2(1H)-yl}(phenyl)acetic acid |

TABLE III-continued

| Structure | Name |
|---|---|
| [structure drawing] | 2-{4-[(1-Methyl-1H-indol-3-yl)methyl]-1-oxophthalazin-2(1H)-yl}pentanoic acid | or a pharmaceutically acceptable salt thereof.

In another embodiment of the invention there is provided the following preferred compounds, in table IV.

TABLE IV

| Name | IC$_{50}$ (nM) |
|---|---|
| {4-[(1-Methyl-1H-indol-3-yl)methyl]-1-oxophthalazin-2(1H)-yl}acetic acid | 300 |
| {4-[(1,4-Dimethyl-1H-indol-3-yl)methyl]-1-oxophthalazin-2(1H)-yl}acetic acid | 50 |
| [4-(Naphthalen-1-ylmethyl)-1-oxophthalazin-2(1H)-yl]acetic acid | 150 |
| 3-{4-[(1,4-Dimethyl-1H-indol-3-yl)methyl]-1-oxophthalazin-2(1H)-yl}propanoic acid | 160 |
| [4-(Naphthalen-1-ylmethyl)-1-oxophthalazin-2(1H)-yl](phenyl)acetic acid | 170 |
| 2-[4-(Naphthalen-1-ylmethyl)-1-oxophthalazin-2(1H)-yl]pentanoic acid | 86 |
| {4-[(1-Methyl-1H-indol-3-yl)methyl]-1-oxophthalazin-2(1H)-yl}(phenyl)acetic acid | 360 |
| 2-{4-[(1,4-Dimethyl-1H-indol-3-yl)methyl]-1-oxophthalazin-2(1H)-yl}pentanoic acid | 9 |
| {4-[(1,4-Dimethyl-1H-indol-3-yl)methyl]-1-oxophthalazin-2(1H)-yl}(phenyl)acetic acid | 7 |
| 2-{4-[(1-Methyl-1H-indol-3-yl)methyl]-1-oxophthalazin-2(1H)-yl}pentanoic acid | 93 | or a pharmaceutically acceptable salt thereof.

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures, and individual diastereomers. All such isomeric forms of these compounds are expressly included in the present invention. Each stereogenic carbon may be in the R or S configuration, or a combination of configurations.

Some of the compounds of formula (I) or (II) can exist in more than one tautomeric form.

The invention includes methods using all such tautomers.

All terms as used herein in this specification, unless otherwise stated, shall be understood in their ordinary meaning as known in the art. For example, $C_{1-4}$alkoxy includes the organic radical $C_{1-4}$alkyl with a terminal oxygen, such as methoxy, ethoxy, propoxy, butoxy.

All organic radicals: alkyl, alkenyl and alkynyl groups, or such groups which are incorporated in other radicals such as acyl and alkoxy, shall be understood as being branched or unbranched where structurally possible and unless otherwise specified, and may be partially or fully halogenated.

The term "lower" referred to above and hereinafter in connection with organic radicals or compounds respectively defines such as branched or unbranched with up to and including 7, preferably up to and including 4 and advantageously one or two carbon atoms.

A cyclic group shall be understood to mean carbocycle, heterocycle or heteroaryl, each may be partially or fully halogenated.

Carbocycles include hydrocarbon rings containing from three to fourteen carbon atoms. These carbocycles may be either aromatic either aromatic or non-aromatic ring systems. The non-aromatic ring systems may be mono- or polyunsaturated, monocyclic, bicyclic or tricyclic and may be bridged. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, benzyl, indanyl, indenyl, benzocyclobutanyl, dihydronaphthyl, tetrahydronaphthyl, naphthyl, decahydronaphthyl, benzocycloheptanyl, adamantyl, norbornyl, fluorene, and benzocycloheptenyl. Certain terms for cycloalkyl such as cyclobutanyl and cyclobutyl shall be used interchangeably.

The term "heteroaryl" shall be understood to mean an aromatic 5-8 membered monocyclic or 8-11 membered bicyclic ring containing 1-4 heteroatoms such as N,O and S. The heteroaryl may be attached by any atom of the ring, which results in the creation of a stable structure. Unless otherwise stated, such heteroaryls include aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, indolyl, benzimidazolyl, benzoxazolyl, benzisoxazolyl, benzopyrrolyl, benzothiazolyl, benzoisothiazolyl, benzothienyl, quinolinyl, quinazolinyl, naphthyridinyl, indazolyl and triazolyl.

The term "heteroatom" as used herein shall be understood to mean atoms other than carbon such as oxygen, nitrogen, sulfur and phosphorous.

As used herein, "nitrogen" and "sulfur" include any oxidized form of nitrogen and sulfur and the quaternized form of any basic nitrogen. All heteroatoms in open chain or cyclic radicals include all oxidized forms.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative and/or is partially or fully halogenated. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I) or (II). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I), (II) or (III).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds described herein are either commercially available or can be made by methods and any necessary intermediates well known in the art.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention also provides processes for making compounds of Formula (I) and (II). In all schemes, unless specified otherwise, R$_1$, R$_2$ and R$_3$ in the formulas below shall have the meaning of R$_1$, R$_2$ and R$_3$ in Formula (I) and (II) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization. The appropriately substituted starting materials and intermediates used in the preparation of compounds of the invention are either commercially available or readily prepared by methods known in the literature to those skilled in the art, and are illustrated in the synthetic examples below.

Compounds of Formula (I) and (II) may be synthesized by the method illustrated in Scheme 1

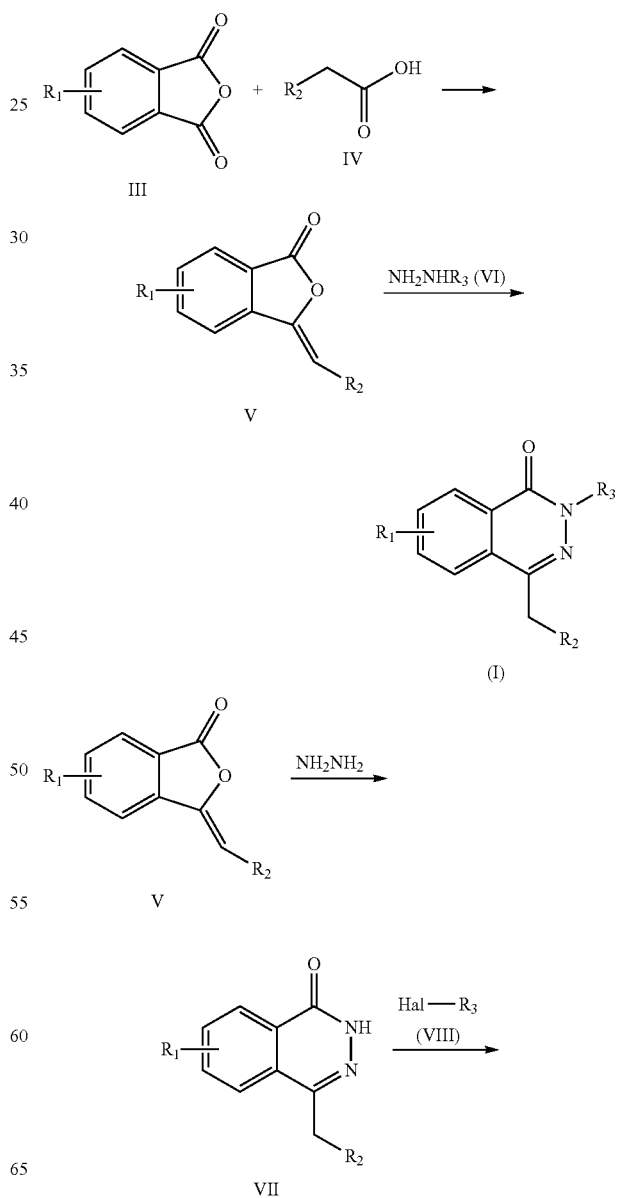

-continued

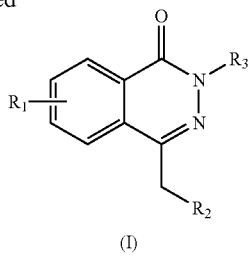

As outlined in Scheme 1, reaction of a phthalic anhydride of formula (III) with an acid of formula (IV), at a suitable temperature provides lactone of formula (V). Reaction of the lactone of formula (V) with a substituted hydrazine of formula (VI), in a suitable solvent, provides a compound of Formula (I).

Alternatively, reaction of the lactone of formula (V) with hydrazine, under suitable conditions, provides a phthalazinone of formula (VII). Alkylation of the phthalazinone (VII) with an alkylating agent, such as Hal-$R_3$ (VIII) wherein Hal=Br or I, in a suitable solvent, in the presence of a suitable base, provides a compound of Formula (I).

The starting acid of formula (IV) wherein $R_2$ is 1,4-dimethyl indolyl, may be synthesized by the method shown in Scheme 2.

potassium cyanide, provides a nitrile of formula (XI). N-methylation of the indole nitrogen in compound (XI) with methyl iodide, under standard reaction conditions, provides the dimethyl indole of formula (XII). Hydrolysis of the nitrile group in compound of formula (XII) provides the desired intermediate of formula (IV), wherein $R_2$ is 1,4 dimethyl indolyl.

Further modification of the initial product of formula (I) or (II) by methods known in the art and illustrated in the Examples below, may be used to prepare additional compounds of this invention.

EXPERIMENTAL

Example 1

[3-(1,4-Dimethyl-1H-indol-3-ylmethyl)-4-eth-(E)-ylidene-6-oxo-5-prop-2-en-(E)-ylidene-5,6-dihydro-4H-pyridazin-1-yl]-acetic acid

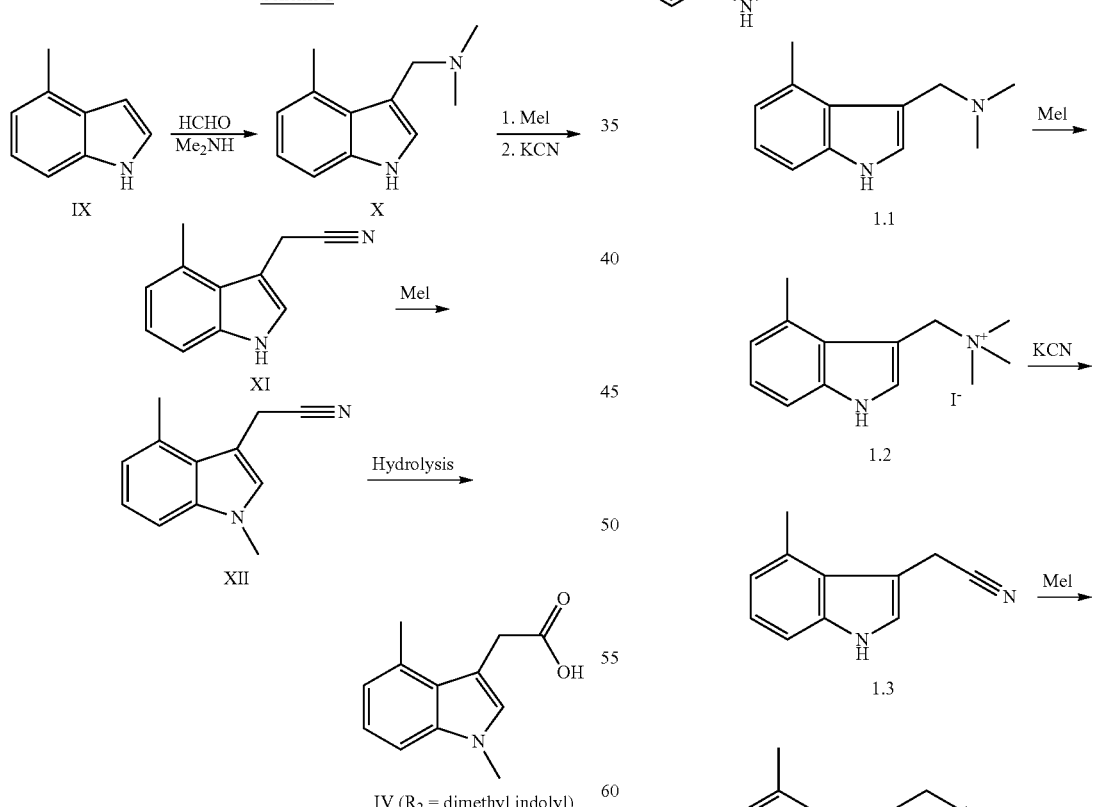

As shown in Scheme 2, reaction of 4-methyl indole (IX) with formaldehyde and dimethyl amine, under suitable reaction conditions, provides a dimethyl amino compound of formula (X). Reaction of the compound of formula (X) with methyl iodide followed by reaction with a reagent such as 23
-continued

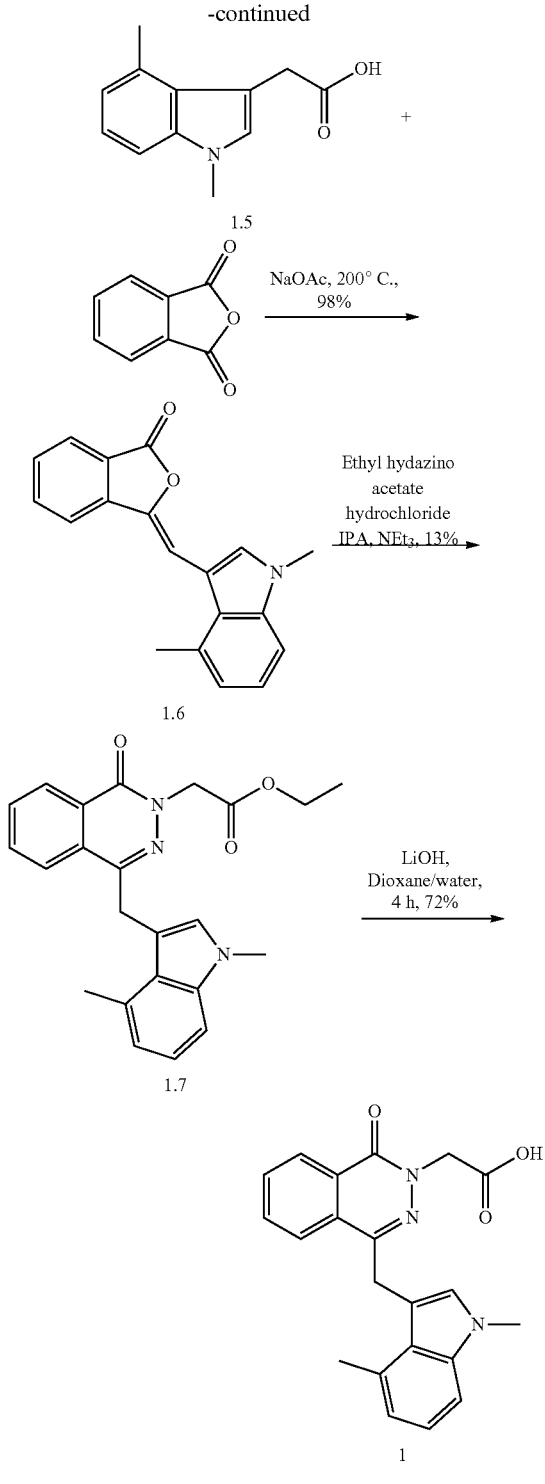

1.1)
Dimethyl-(4-methyl-1H-indol-3-ylmethyl)-amine

To a chilled solution of dimethyl amine (30 mL, 40% in water, 120 mmol) and formalin (13 mL, 37% in water, 84 mmol) in glacial acetic acid (30 mL) is added 4-methyl indole (21 g, 165 mmol) at 0° C. The reaction is warmed to room temperature and stirred for 3 hours. The reaction mixture is brought to pH 12 by addition of 50% NaOH and ice, and the product extracted with methylene chloride. The organic layers are dried over $Na_2SO_4$ filtered and evaporated in vacuo to give the title compound that is used without further purification (33 g, 162 mmol, 98%) LC/MS ($M^+$+1): 205.7.

1.2)
Trimethyl-(4-methyl-1H-indol-3-ylmethyl)-ammonium iodide

Dimethyl-(4-methyl-1H-indol-3-ylmethyl)-amine (20 g, 98 mmol) is suspended in acetonitrile, and warmed to completely dissolve the material. The reaction is cooled to room temperature and then methyl iodide (9.1 mL, 147 mmol) is added dropwise to the reaction. The reaction is covered with foil and then stirred at room temperature overnight. The reaction is then filtered and the filtrate evaporate in vacuo to give an oil that is taken up in acetonitrile. The white solid is then triturated with acetonitrile and ether, and combined with the original solid to give the title compound that is used without further purification (30 g, 87 mmol, 88%) LC/MS ($M^+$+1): 347.

1.3) (4-Methyl-1H-indol-3-yl)-acetonitrile

Trimethyl-(4-methyl-1H-indol-3-ylmethyl)-ammonium iodide (2.6 g, 7.5 mmol) is suspended in ethanol (53 mL) and sodium cyanide (736 mg, 15 mmol), is added to the reaction. The reaction is stirred and heated to reflux overnight. After 16 hours the reaction is cooled to room temperature and evaporated in vacuo. The resulting oil is taken up in dichloromethane and washed with water 3×, dried ($Na_2SO_4$), filtered and evaporated in vacuo. The resulting material is purified on silica with hexanes/dichloromethane as the eluent (1.0 g, 5 mmol, 71%) LC/MS ($M^+$+1): 171.3.

1.4) (1,4-Dimethyl-1H-indol-3-yl)-acetonitrile (4-Methyl-1H-indol-3-yl)-acetonitrile (540 mg, 3.2 mmol), is taken up in dry THF (10.3 mL), cooled to zero, and sodium hydride (228 mg, 60% in mineral oil, 6 mmol) is added to the stirring solution. The reaction is stirred for 15 minutes at zero and methyl iodide (0.26 mL, 4 mmol) is added. The solution is stirred for 20 minutes at zero, and quenched by the slow addition of saturated aqueous ammonium chloride. The compound is extracted with ethyl acetate, dried ($Na_2SO_4$), filtered, and evaporated in vacuo to give a solid that is purified on silica gel with hexanes/ethylacetate as the eluent (1.0 g, 5 mmol, 71%) LC/MS ($M^+$+1): 185.5.

1.5) (1,4-Dimethyl-1H-indol-3-yl)-acetic acid (1,4-Dimethyl-1H-indol-3-yl)-acetonitrile (6.0 g, 33 mmol) is suspended in ethanol (150 mL) and then potassium hydroxide (10.6 g, 162 mmol) in water (150 mL) is added to the solution. The reaction is stirred and then heated to reflux for 16 hours. the reaction is then cooled to room temperature and diluted with water. The aqueous layer is washed with DCM (3×150 mL) and then the water layer is cooled to zero and acidified with the addition of 12N HCl. The resulting suspension is extracted with DCM (3×100 mL) and the organic layers are combined, filtered and evaporated in vacuo. The resulting product is used without further purification (3.9 g, 20 mmol, 60%) LC/MS ($M^+$+1): 204.7.

1.6) 3-[1-(1,4-Dimethyl-1H-indol-3-yl)-meth-(Z)-ylidene]-3H-isobenzofuran-1-one A reaction flask equipped with a nitrogen line and a stir bar is charged with (1,4-Dimethyl-1H-indol-3-yl)-acetic acid (0.5 g, 2.4 mmol), 0.3 g (2.4 mmol) of phthalic anhydride followed by 1.2 g (15.2 mmol) of anhydrous sodium acetate. The flask is heated to 200° C. under a stream of nitrogen for 2 h. Water formed is azeotropically evaporated using toluene. The resulting brown melt (98%) is taken immediately to the next step LC/MS (M$^+$+1): 290.3.

1.7) [4-(1,4-Dimethyl-1H-indol-3-ylmethyl)-1-oxo-1H-phthalazin-2-yl]-acetic acid ethyl ester A reaction flask equipped with a nitrogen line and a stir bar is charged with 1.6 (0.7 g, 2.4 mmol) in 4 mL of IPA. 0.6 g (5.0 mmol) of ethyl hydazinoacetate hydrochloride followed by 7.2 mL (5.0 mmol) of triethylamine is added. The reaction is refluxed for 4 h at 100° C. The solvent is removed and is dissolved in 10% methanol/dichloromethane. The organic layer is washed with water (1×) and brine (1×). The organic layer is dried over anhydrous sodium sulfate. The solvent is evaporated and the resulting solid is purified by reversed phase HPLC eluting with 5-95% acetonitrile/water to give 1.7 (0.13 g, 13%) LC/MS (M$^+$+1): 390.2.

1) [3-(1,4-Dimethyl-1H-indol-3-ylmethyl)-4-eth-(E)-ylidene-6-oxo-5-prop-2-en-(E)-ylidene-5,6-dihydro-4H-pyridazin-1-yl]-acetic acid A reaction flask equipped with a nitrogen line and a stir bar is charged with 45 mg (0.12 mmol) of 1.7 in 4 ml of dioxane/water (1:1). 9.7 mg (0.23 mmol) of lithium hydroxide is added and stirred for 4 hours. The solvent is evaporated and is diluted with dichloromethane and water. The organic layer discarded. Aqueous layer acidified with 5% HCl to a pH of 3. Desired product extracted with dichloromethane. Organic layer dried with anhydrous sodium sulfate and the solvent evaporated to give the title compound 1 (30 mg, 72%) LC/MS (M$^+$+1): 362.2.

2) [3-(2-naphthyl)-4-eth-(E)-ylidene-6-oxo-5-prop-2-en-(E)-ylidene-5,6-dihydro-4H-pyridazin-1-yl]-propionic acid This is made in a analogous fashion to example 1 starting with 2 naphthyl acetic acid, and ring expansion with ethylhydrazinopropionate hydrochloride, and saponification to give the title compound. 9% overall yield, LC/MS (M$^+$+1): 359.2.

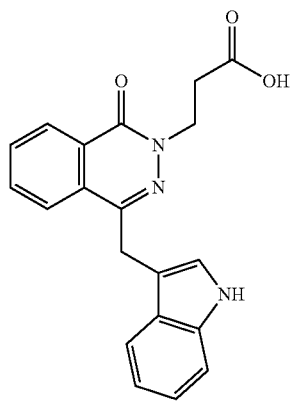

3) [3-(1H-indol-3-ylmethyl)-4-eth-(E)-ylidene-6-oxo-5-prop-2-en-(E)-ylidene-5,6-dihydro-4H-pyridazin-1-yl]-propionic acid This is made in a analogous fashion to example 1 starting with 2 1-H indole acetic acid, ring expansion with ethylhydrazinopropionate hydrochloride, and saponification to give the title compound. 4% overall yield, LC/MS (M$^+$+1): 348.3.

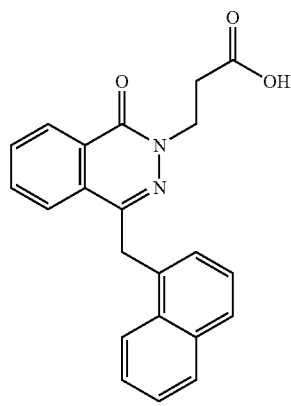 [SMILES: O=C(O)CCn1nc(Cc2cccc3ccccc23)c2ccccc2c1=O]

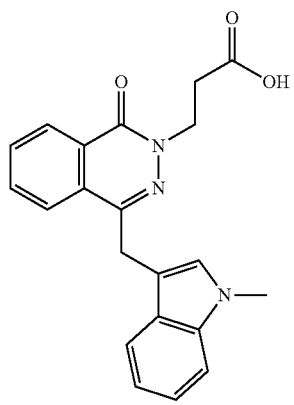 [SMILES: Cn1cc(Cc2nn(CCC(=O)O)c(=O)c3ccccc23)c2ccccc21]

4) [3-(1-Methyl-1H-indol-3-ylmethyl)-4-eth-(E)-ylidene-6-oxo-5-prop-2-en-(E)-ylidene-5,6-dihydro-4H-pyridazin-1-yl]-propionic acid This is made in a analogous fashion to example 1 starting with 2-(1-Methyl indole) acetic acid, ring expansion with ethylhydrazinopropionate hydrochloride, and saponification to give the title compound. 3.4% overall yield, LC/MS (M$^+$+1): 362.2

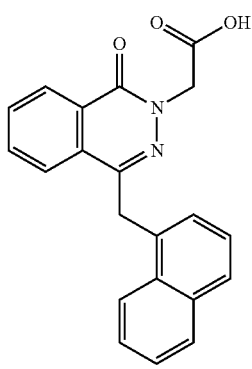 [SMILES: O=C(O)Cn1nc(Cc2cccc3ccccc23)c2ccccc2c1=O]

5) [3-(2-naphthyl)-4-eth-(E)-ylidene-6-oxo-5-prop-2-en-(E)-ylidene-5,6-dihydro-4H-pyridazin-1-yl]-acetic acid This is made in a analogous fashion to example 1 starting with 2 naphthyl acetic acid, and ring expansion with ethylhydrazinoacetate hydrochloride, and saponification to give the title compound. 9.8% overall yield, LC/MS (M$^+$+1): 345.2.

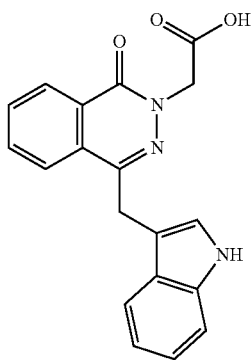 [SMILES: O=C(O)Cn1nc(Cc2c[nH]c3ccccc23)c2ccccc2c1=O]

6) [3-(1H-indol-3-ylmethyl)-4-eth-(E)-ylidene-6-oxo-5-prop-2-en-(E)-ylidene-5,6-dihydro-4H-pyridazin-1-yl]-acetic acid This is made in a analogous fashion to example 1 starting with 2 1-H indole acetic acid, ring expansion with ethylhydrazinoacetate hydrochloride, and saponification to give the title compound. 1.5% overall yield, LC/MS (M$^+$+1): 334.2.

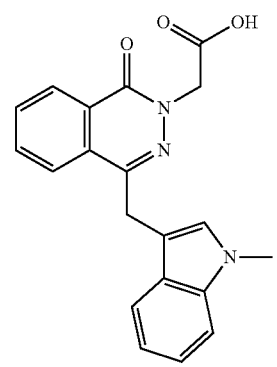 [SMILES: Cn1cc(Cc2nn(CC(=O)O)c(=O)c3ccccc23)c2ccccc21]

7) [3-(1-Methyl-1H-indol-3-ylmethyl)-4-eth-(E)-ylidene-6-oxo-5-prop-2-en-(E)-ylidene-5,6-dihydro-4H-pyridazin-1-yl]-acetic acid This is made in a analogous fashion to example 1 starting with 2-(1-Methyl indole) acetic acid, ring expansion with ethylhydrazinoacetate hydrochloride, and saponification to give the title compound. 3% overall yield, LC/MS (M$^+$+1): 348.1

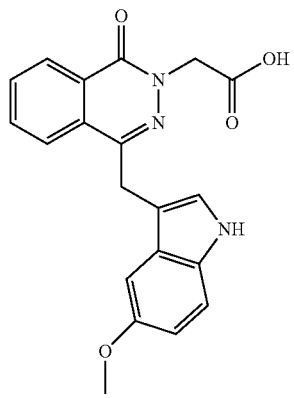 [SMILES: COc1ccc2[nH]cc(Cc3nn(CC(=O)O)c(=O)c4ccccc34)c2c1]

8) [3-(5-Methoxy-1H-indol-3-ylmethyl)-4-eth-(E)-ylidene-6-oxo-5-prop-2-en-(E)-ylidene-5,6-dihydro-4H-pyridazin-1-yl]-acetic acid This is made in a analogous fashion to example 1 starting with 2-(5-Methoxy-1H indole) acetic acid, ring expansion with ethylhydrazinoacetate hydrochloride, and saponification to give the title compound. 0.6% overall yield, LC/MS (M$^+$+1): 364.2.

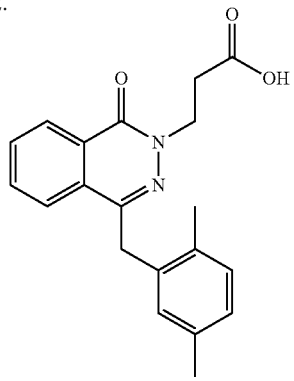

9) [3-(2,5-Dimethylphenyl acetic acid)-4-eth-(E)-ylidene-6-oxo-5-prop-2-en-(E)-ylidene-5,6-dihydro-4H-pyridazin-1-yl]-propionic acid This is made in a analogous fashion to example 1 starting with 2,5 Dimethyl phenylacetic acid, ring expansion with ethylhydrazinopropionate hydrochloride, and saponification to give the title compound. 7.7% overall yield, LC/MS (M$^+$+1): 337.2.

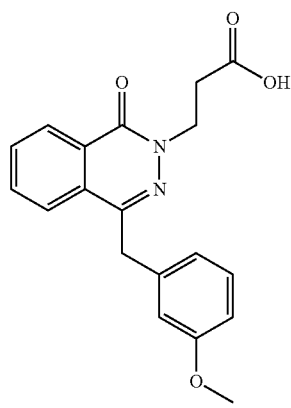 [SMILES: COc1cccc(Cc2nn(CCC(=O)O)c(=O)c3ccccc23)c1]

10) [3-(3-Methoxyphenylacetic acid)-4-eth-(E)-ylidene-6-oxo-5-prop-2-en-(E)-ylidene-5,6-dihydro-4H-pyridazin-1-yl]-propionic acid This is made in a analogous fashion to example 1 starting with 3-Methoxyphenylacetic acid, ring expansion with ethylhydrazinopropionate hydrochloride, and saponification to give the title compound. 3% overall yield, LC/MS (M$^+$+1): 339.3.

Example 11

[3-(1,4-Dimethyl-1H-indol-3-ylmethyl)-5-eth-(E)-ylidene-6-oxo-4-prop-2-en-(E)-ylidene-5,6-dihydro-4H-pyridazin-1-yl]-phenyl-acetic acid

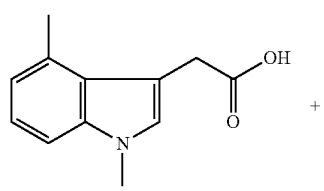

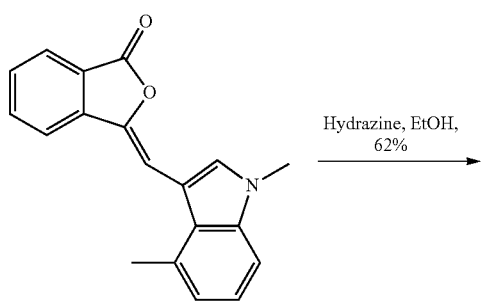

11.1

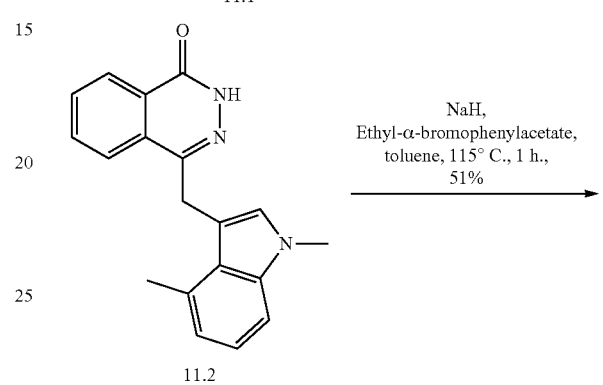

11.2

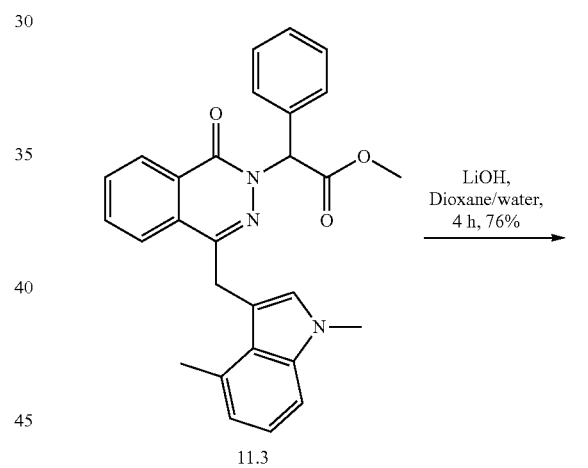

11.3

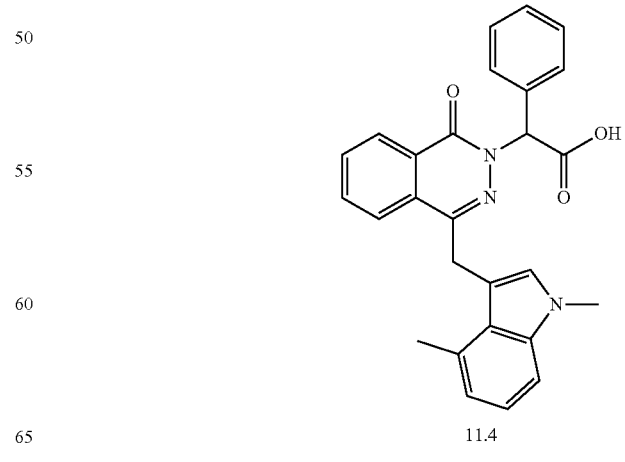

11.4

11.1) 3-[1-(1,4-Dimethyl-1H-indol-3-yl)-meth-(Z)-ylidene]-3H-isobenzofuran-1-one A reaction flask equipped with a nitrogen line and a stir bar is charged with (1,4-Dimethyl-1H-indol-3-yl)-acetic acid (0.5 g, 2.4 mmol) (from example 1.5), 0.3 g (2.4 mmol) of phthalic anhydride followed by 1.2 g (15.2 mmol) of anhydrous sodium acetate. The flask is heated to 200° C. under a stream of nitrogen for 2 h. Water formed is azeotropically evaporated using toluene. The resulting brown melt 11.1 (98%) is taken immediately to the next step LC/MS ($M^++1$): 290.3.

11.2) 4-(1,4-Dimethyl-1H-indol-3-ylmethyl)-2H-phthalazin-1-one

A reaction flask equipped with a nitrogen line and a stir bar is charged with 120 mg (0.4 mmol) of 11.1 in 4 ml of ethanol. 65% Hydrazine monohydrate (52 µL/0.4 mmol) is added. The reaction mixture is refluxed for 3 h. The product precipitated. The reaction mixture filtered and the residue washed with 2 mL of ethanol. Resulting white powder is dried to give 11.2 (78 mg, 62%) LC/MS ($M^++1$): 304.4.

11.3) [4-(1,4-Dimethyl-1H-indol-3-ylmethyl)-1-oxo-1H-phthalazin-2-yl]-phenyl-acetic acid ethyl ester A reaction flask equipped with a nitrogen line and a stir bar is charged with 4.3 mg (0.1 mmol) of 60% sodium hydride in mineral oil. 11.2 (33 mg, 0.1 mmol) in 4 mL of toluene is added. The reaction mixture is refluxed for 1 h. The reaction mixture is allowed to slowly cool to room temperature. 16.6 µL (0.1 mmol) of methyl-α-bromo phenylacetate is added. The reaction mixture is refluxed for further 24 h. The reaction mixture is quenched with 5% HCl. The solvent is evaporated and the resulting crude product is dissolved in 1 mL of DMSO. The crude product is purified by reversed phase HPLC eluting with 5-95% AcCN/water to give 11.3 (25 mg, 51%) LC/MS ($M^++1$): 452.3.

11) [3-(1,4-Dimethyl-1H-indol-3-ylmethyl)-5-eth-(E)-ylidene-6-oxo-4-prop-2-en-(E)-ylidene-5,6-dihydro-4H-pyridazin-1-yl]-phenyl-acetic acid A reaction flask equipped with a nitrogen line and a stir bar is charged with 15 mg (0.03 mmol) of 3 in 4 ml of dioxane/water (1:1). 2.7 mg (0.06 mmol) of lithium hydroxide is added and the reaction stirred at room temperature for 4 hours. The solvent is evaporated and is diluted with dichloromethane and water. The organic layer discarded. Aqueous layer acidified with 5% HCl to a pH of 3. Desired product extracted with dichloromethane. Organic layer is dried with anhydrous sodium sulfate and the solvent evaporated to give 11.4 (11 mg, 76%) LC/MS ($M^++1$): 438.3.

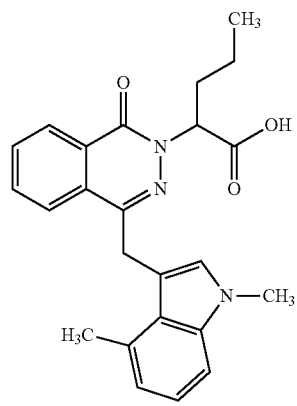 [SMILES: CCCC(C(=O)O)n1nc(Cc2cn(C)c3cccc(C)c23)c2ccccc2c1=O]

12) [3-(1,4-Dimethyl-1H-indol-3-ylmethyl)-5-eth-(E)-ylidene-6-oxo-4-prop-2-en-(E)-ylidene-5,6-dihydro-4H-pyridazin-1-yl]-propyl-acetic acid This is made in a analogous fashion to example 11 starting with 1,4-Dimethyl-indol-3-acetic acid, ring expansion with hydrazine hydrochloride, alkylation with ethyl-alpha-bromopentanoic acid, and saponification to give the title compound. 15% overall yield, LC/MS ($M^++1$): 404.3.

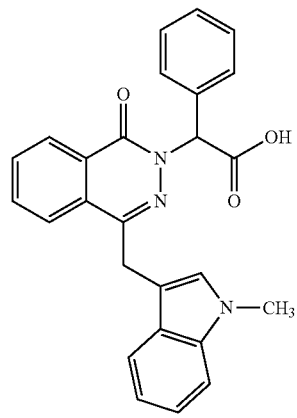 [SMILES: Cn1cc(Cc2nn(C(C(=O)O)c3ccccc3)c(=O)c3ccccc23)c2ccccc21]

13) [3-(1-Methyl-1H-indol-3-ylmethyl)-5-eth-(E)-ylidene-6-oxo-4-prop-2-en-(E)-ylidene-5,6-dihydro-4H-pyridazin-1-yl]-phenyl-acetic acid This is made in a analogous fashion to example 11 starting with 1-Methyl-indol-3-acetic acid, ring expansion with hydrazine hydrochloride, alkylation with Ethyl-alpha-bromophenylacetate, and saponification to give the title compound. 1% overall yield, LC/MS ($M^++1$): 424.4.

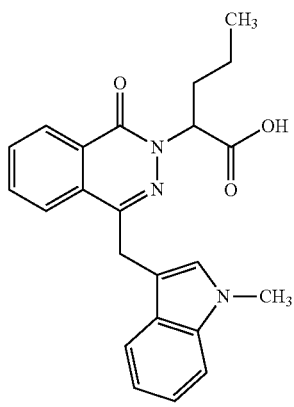 [SMILES: CCCC(C(=O)O)n1nc(Cc2cn(C)c3ccccc23)c2ccccc2c1=O]

14) [3-(1-Methyl-1H-indol-3-ylmethyl)-5-eth-(E)-ylidene-6-oxo-4-prop-2-en-(E)-ylidene-5,6-dihydro-4H-pyridazin-1-yl]-propyl-acetic acid This is made in a analogous fashion to example 11 starting with 1-Methyl-indol-3-acetic acid, ring expansion with hydrazine hydrochloride, alkylation with ethyl-alpha-bromopentanoic acid, and saponification to give the title compound. 1.6% overall yield, LC/MS (M$^+$+1): 390.3.

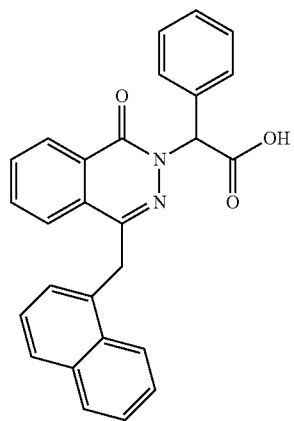 [SMILES: O=C(O)C(c1ccccc1)n1nc(Cc2cccc3ccccc23)c2ccccc2c1=O]

15) [3-(2-naphthyl)-5-eth-(E)-ylidene-6-oxo-4-prop-2-en-(E)-ylidene-5,6-dihydro-4H-pyridazin-1-yl]-phenyl-acetic acid This is made in a analogous fashion to example 11 starting with 2-Naphthyl acetic acid, ring expansion with hydrazine hydrochloride, alkylation with Ethyl-alpha-bromophenylacetate, and saponification to give the title compound. 16.4% overall yield, LC/MS (M$^+$+1): 421.4.

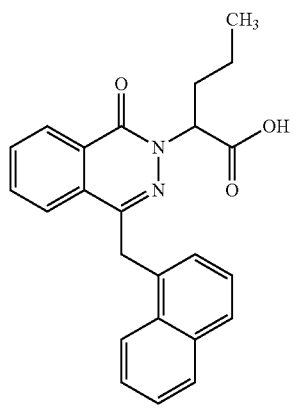 [SMILES: CCCC(C(=O)O)n1nc(Cc2cccc3ccccc23)c2ccccc2c1=O]

16) [3-(2-Naphthyl)-5-eth-(E)-ylidene-6-oxo-4-prop-2-en-(E)-ylidene-5,6-dihydro-4H-pyridazin-1-yl]-propyl-acetic acid This is made in a analogous fashion to example 11 starting with 2-Naphthylacetic acid, ring expansion with hydrazine hydrochloride, alkylation with ethyl-alpha-bromopentanoic acid, and saponification to give the title compound. 23% overall yield, LC/MS (M$^+$+1): 387.3

In a similar fashion the following compounds can be made:

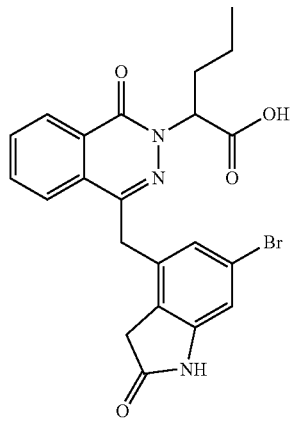 [SMILES: CCCC(C(=O)O)n1nc(Cc2cc(Br)cc3c2CC(=O)N3)c2ccccc2c1=O]

2-[4-(6-Bromo-2-oxo-2,3-dihydro-1H-indol-4-ylmethyl)-1-oxo-1H-phthalazin-2-yl]-pentanoic acid

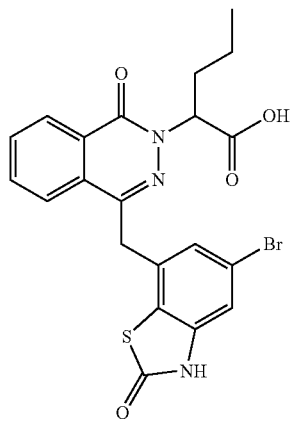 [SMILES: CCCC(C(=O)O)n1nc(Cc2cc(Br)cc3[nH]c(=O)sc23)c2ccccc2c1=O]

35
2-[4-(5-Bromo-2-oxo-2,3-dihydro-benzothiazol-7-ylmethyl)-1-oxo-1H-phthalazin-2-yl]-pentanoic acid 36
2-[4-(4,6-Dimethyl-benzo[d]isothiazol-3-ylmethyl)-1-oxo-1H-phthalazin-2-yl]-pentanoic acid

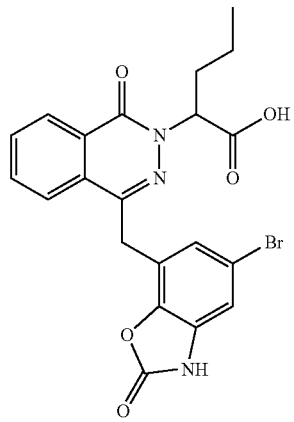 [SMILES: CCCC(C(=O)O)n1nc(Cc2cc(Br)cc3[nH]c(=O)oc23)c2ccccc2c1=O]

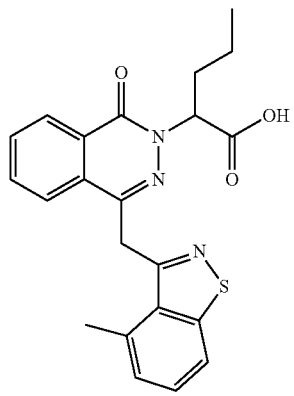 [SMILES: CCCC(C(=O)O)n1nc(Cc2nsc3cccc(C)c23)c2ccccc2c1=O]

2-[4-(5-Bromo-2-oxo-2,3-dihydro-benzooxazol-7-ylmethyl)-1-oxo-1H-phthalazin-2-yl]-pentanoic acid 2-[4-(4-Methyl-benzo[d]isothiazol-3-ylmethyl)-1-oxo-1H-phthalazin-2-yl]-pentanoic acid

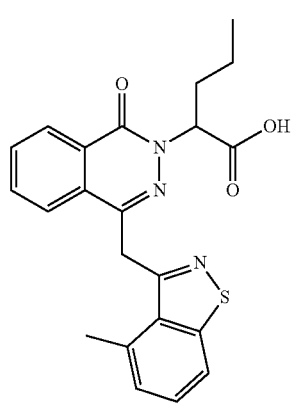 [SMILES: CCCC(C(=O)O)n1nc(Cc2nsc3cccc(C)c23)c2ccccc2c1=O]

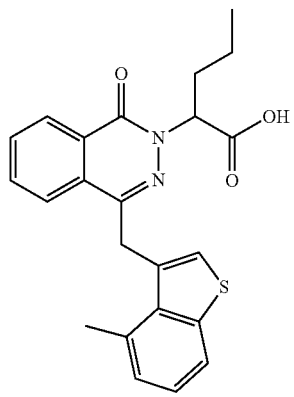 [SMILES: CCCC(C(=O)O)n1nc(Cc2csc3cccc(C)c23)c2ccccc2c1=O]

2-[4-(4-Methyl-benzo[d]isothiazol-3-ylmethyl)-1-oxo-1H-phthalazin-2-yl]-pentanoic acid 2-[4-(4-Methyl-benzo[b]thiophen-3-ylmethyl)-1-oxo-1H-phthalazin-2-yl]-pentanoic acid

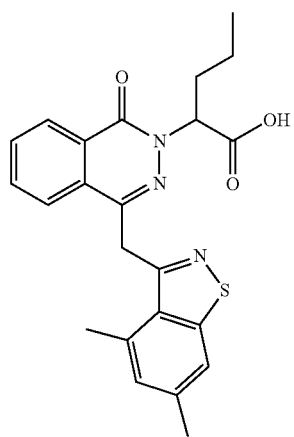

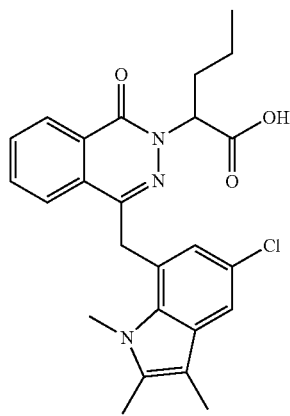 [SMILES: CCCC(C(=O)O)n1nc(Cc2cc(Cl)cc3c(C)c(C)n(C)c23)c2ccccc2c1=O]

2-[4-(5-Chloro-1,2,3-trimethyl-1H-indol-7-ylm-ethyl)-1-oxo-1H-phthalazin-2-yl]-pentanoic acid Methods of Use In accordance with the invention, there are provided methods of using the compounds as described herein and their pharmaceutically acceptable derivatives. The compounds used in the invention inhibit Chymase. Since Chymase is known to transform angiotensin I to angiotensin II and may contribute to activation of TGF-β, matrix proteases and cytokines, the inhibition of Chymase is an attractive means for preventing and treating a variety of diseases or conditions. Examples include heart failure including chronic heart failure (non-ischemic), post-myocardial infarction heart failure (ischemic), acute myocardial infarction, reperfusion injury, left ventricular dysfunction, cardiac fibrosis, diastolic heart failure and hypertrophic cardiomyopathy, hypertension including pulmonary hypertension, systolic hypertension and resistant hypertension, including coronary artery disease, peripheral arterial occlusive disease, aneurism, stable/unstable angina, restenosis, diabetic nephropathy, atrial fibrillation/ventricular arrhythmias, valvular heart disease, pericardial diseases, renal insufficiency (chronic kidney disease, end stage renal disease), stroke. The compounds of the invention may also be useful for the following procedures: coronary artery bypass grafting, percutaneous coronary intervention and stenting.

Other diseases within the scope of the invention include allergic rhinitis, dermatitis, chronic obstructive pulmonary disease (COPD), and pulmonary inflammation, asthma, osteoarthritis, bone resorption diseases, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, inflammatory bowel diseases, acute and chronic pain as well as symptoms of inflammation, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopheresis, granulocyte transfusion associated syndromes, and necrotizing entrerocolitis, traumatic arthritis, and sepsis. Reference in this regard may be made to U.S. Pat. No. 5,948,785; U.S. Pat. No. 6,271,238; U.S. Pat. No. 5,691,335; U.S. Pat. No. 5,814,631; U.S. Pat. No. 6,300,337; EP 1,099,690; U.S. Pat. No. 6,323,219; US 2005-0245536 A1; Fukami, et al., *Current Pharmaceutical Design* 1998, vol. 4, pp. 439-453.

As disclosed in the Background of the Invention, the compounds of the invention may contribute to activation of cytokines, they will therefore be useful for treating oncological diseases. Reference in this regard may be made to US 2005-0245536 A1. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypothalamic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds described herein may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Combinations with other therapeutics include but are not limited to: angiotensin II receptor blockers, angiotensin converting enzyme inhibitors, CETP inhibitors/apoA1 mimetics, adenosine diphosphate (P2Y12) inhibitors, direct thrombin inhibitors, aldosterone antagonists, factor Xa inhibitors, natriuretic peptides (ANP/BNP), renin inhibitors, anti-arrhythmics, Chymase inhibitors, HMG-CoA Reductase inhibitors (Statins), Rho kinase inhibitors, beta-blockers, Lipoprotein-associated phospholipase A2 inhibitors, cardiac glycosides, calcium channel blockers, diuretics, fibrates, Endothelin Receptor Antagonists, GPIIb/IIIa inhibitors, histone deacetylase inhibitors, heparins, nicotinic acid derivatives, vasopeptidase inhibitors, nitrites and nitrates, fatty acid oxidation inhibitors, oral anticoagulants, acyl-CoA:cholesterol acyltransferase inhibitors, thrombolytics, microsomal triglyceride transfer protein inhibitors, thiazolidinediones, adenosine receptor modulators, cholesterol absorption inhibitors, Advanced Glycation End products/receptor (AGE/RAGE) interaction modulators/blockers, acetyl salicylic acid, dipyridamole, gene therapy and cell therapy.

Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the above-described compounds include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:

(i) preventing the disease-state from occurring in a patient, in particular, when such patient is genetically or otherwise predisposed to the disease-state but has not yet been diagnosed as having it;

(ii) inhibiting or ameliorating the disease-state in a patient, i.e., arresting or slowing its development; or (iii) relieving the disease-state in a patient, i.e., causing regression or cure of the disease-state.

In Vitro Assay for Inhibition of Chymase

Chymase assays were performed in a total volume of 15 µL in Corning black opaque 384-well microtiter plates with a non-binding surface (Corning, N.Y.). The assay buffer was comprised of 20 mM Tris HCl pH 8.0, 50 mM NaCl, 0.01% CHAPS. The test compounds were serially diluted 3-fold with neat DMSO in a 96-well polypropylene plate from a 10 mM DMSO stock to give the 10 point dose response curve. 3 µL of the resulting DMSO solution were transferred to a 384-well polypropylene plate in duplicate, and 37 µL of assay buffer was added. Chymase was added to the assay plate in 3 uL of assay buffer followed by 2 uL of the appropriate compound dilution using a PlateMate Plus (Matrix Technologies Corp., Hudson, N.H.). The reaction was initiated by the addition of 10 uL rhodamine 110, bis-(succinoyl-L-alanyl-L-alanyl-L-prolyl-L-phenylalanylamide) (American Peptides, Sunnyvale, Calif.) in assay buffer containing 150 µM tris(2-carboxyethyl)phosphine (TCEP, Pierce Chemical, Rockford, Ill.) using a Multidrop (Thermo Electron Corp., Waltham, Mass.). Final assay concentrations were 500 µM chymase, 100 nM substrate, 100 µM TCEP, and 1% DMSO. The plates were incubated at 28° C. and 80% humidity for 1 hour, at which time the fluorescence was read on a Viewlux 1430 Microplate Imager (Perkin Elmer Life Sciences, Boston, Mass.) with 485 nm excitation, 530 nm emission, and a fluorescein dichroic mirror. The percentage of control values were calculated relative to assay blanks containing complete reaction minus chymase and a 100% control containing assay buffer with 1% DMSO in place of compound. IC50 values were obtained by fitting the data using XLFit4 (IDBS Software).

Preferred compounds of the invention have an activity of 1 microMolar or less.

All patent and literature references cited in this application are incorporated herein by reference in their entirety.

The invention claimed is:
1. A compound chosen from
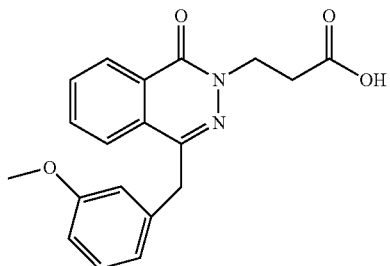
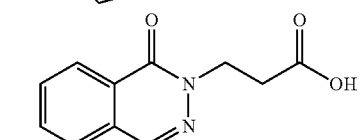
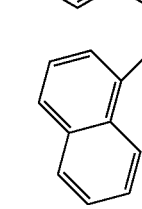
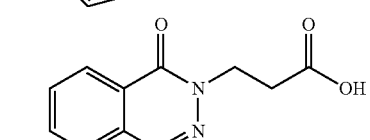
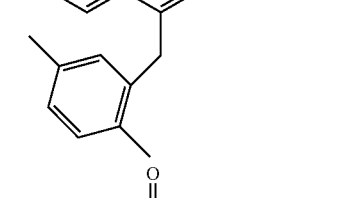
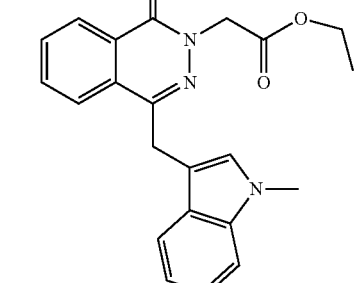
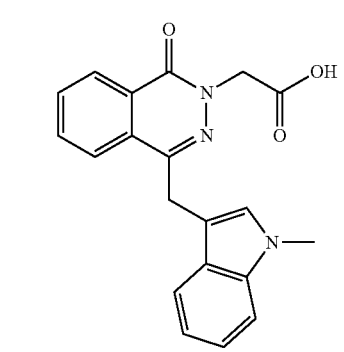
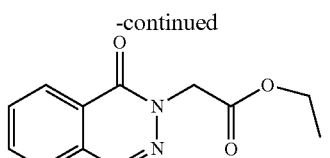
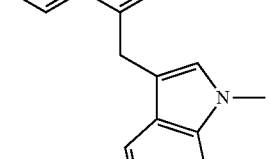
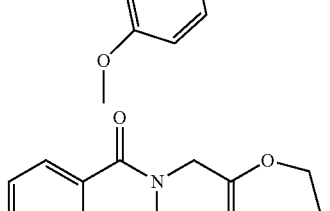
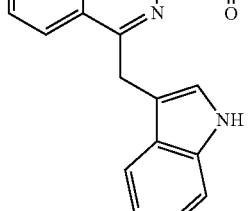
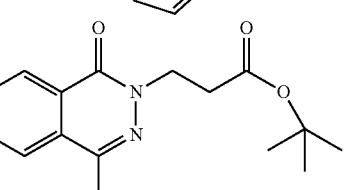
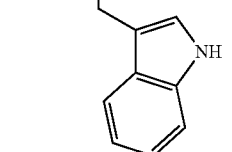
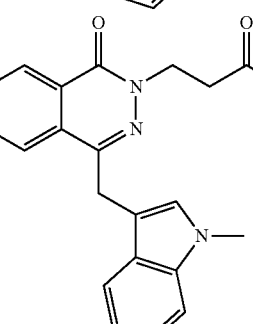
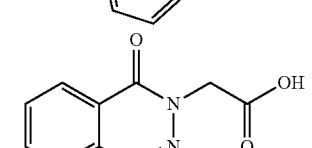
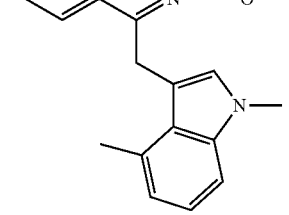

43
-continued
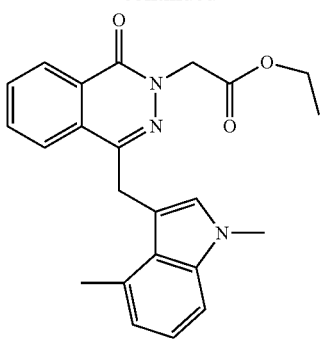
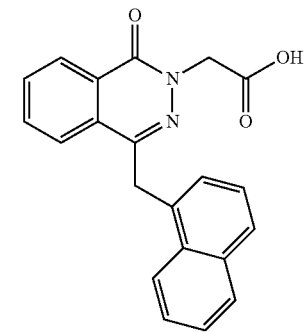
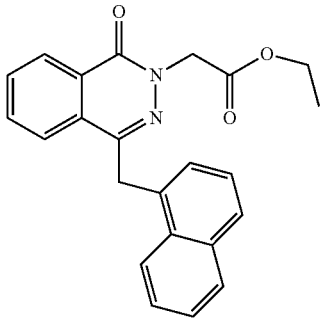
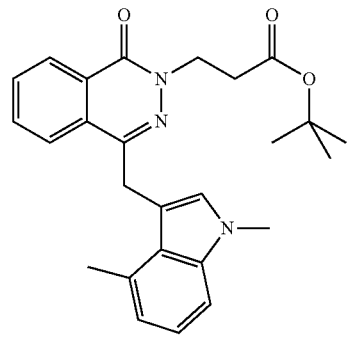
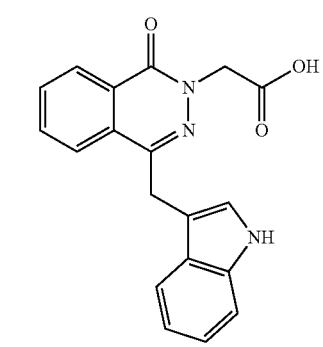
44
-continued
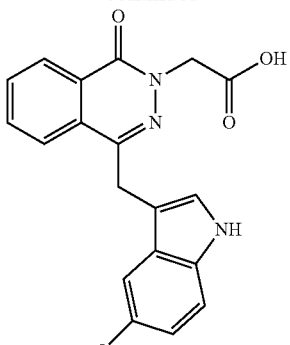
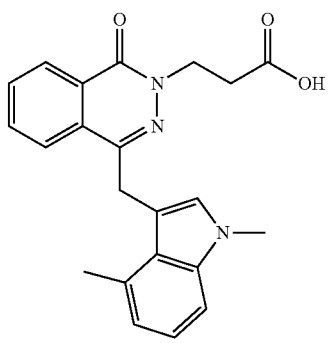
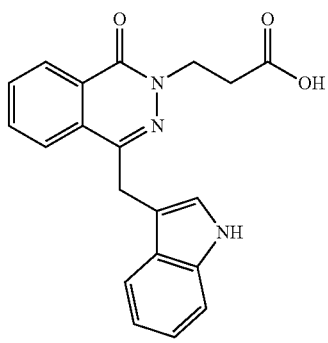
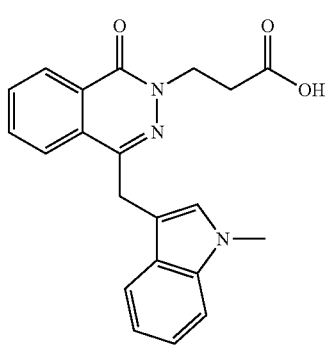

-continued

-continued
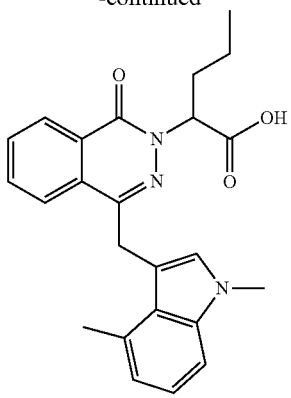
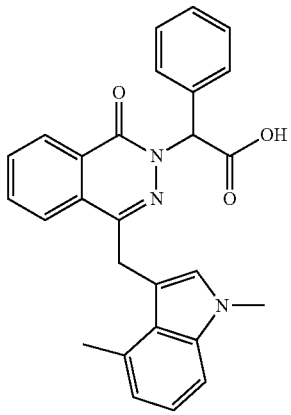
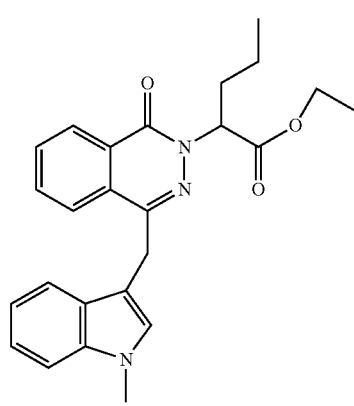
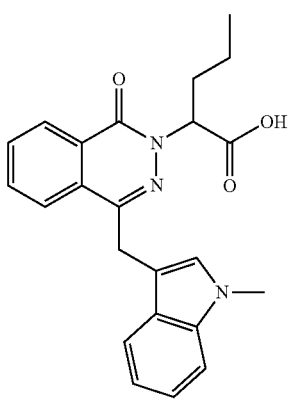
-continued
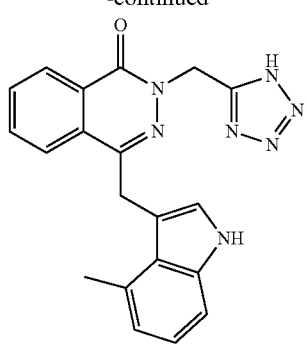
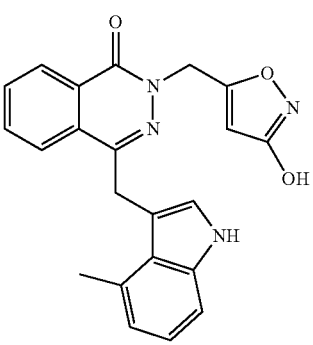
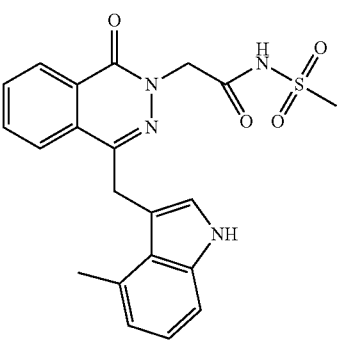
or a pharmaceutically acceptable salt thereof.
2. A compound chosen from
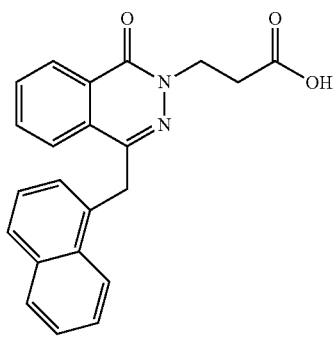

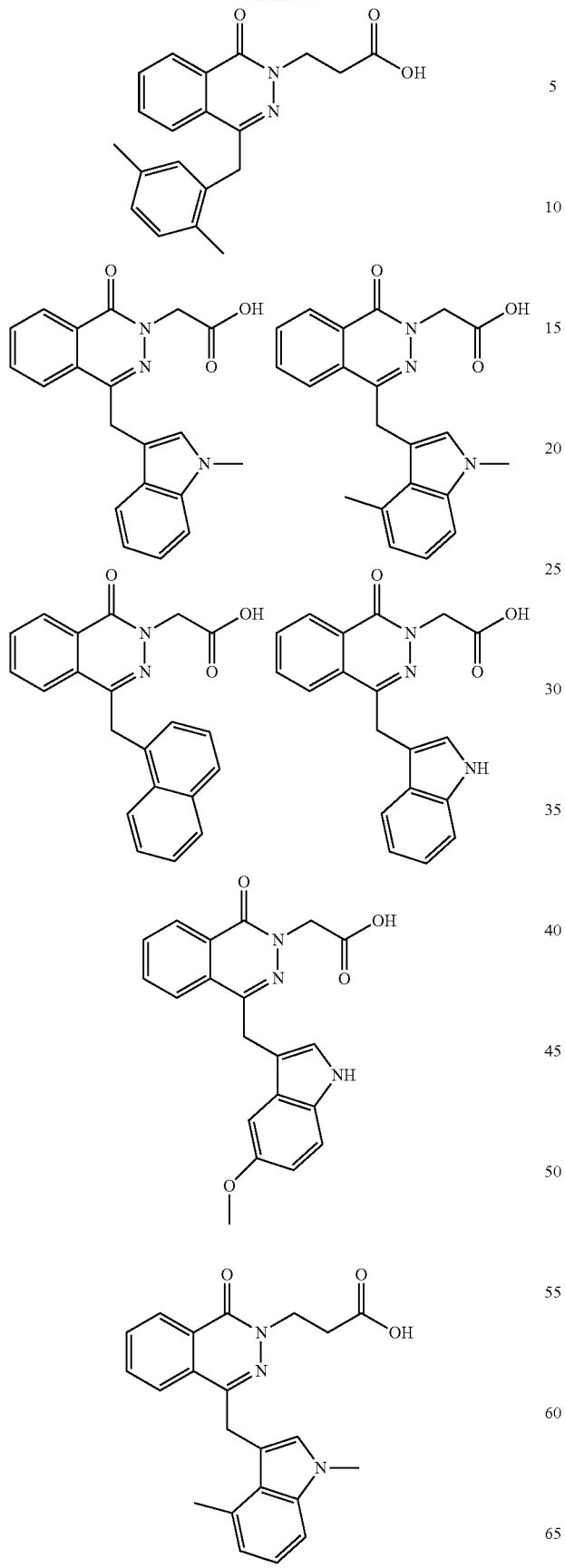

51
-continued
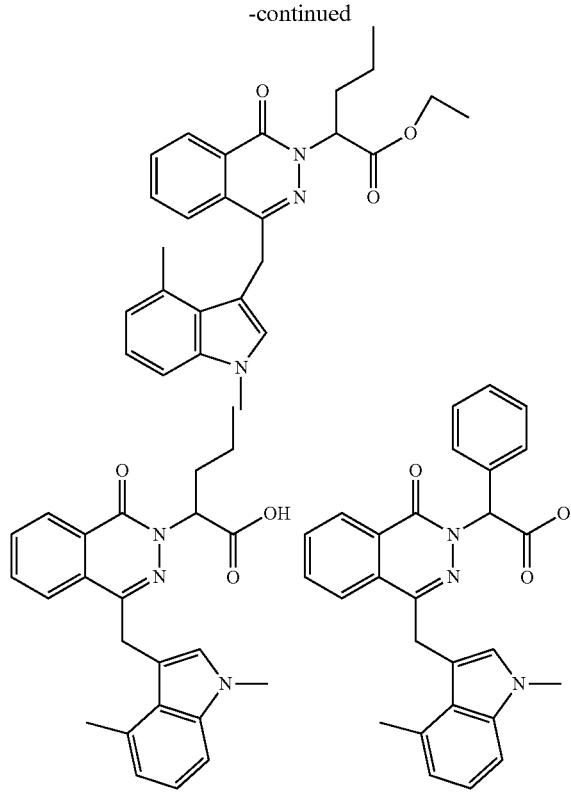
52
-continued
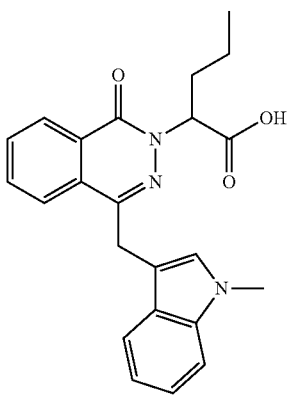
or a pharmaceutically acceptable salt thereof.
3. A pharmaceutical composition comprising a therapeutically effective amount of a compound according to claim 1 and one or more pharmaceutically acceptable carries and/or adjuvants.
* * * * *